United States Patent [19]
Yoshikawa

[11] 4,257,256
[45] Mar. 24, 1981

[54] ULTRASONIC CROSS-SECTIONAL IMAGING APPARATUS

[75] Inventor: Noriaki Yoshikawa, Yokohama, Japan

[73] Assignee: Tokyo Shibaura Denki Kabushiki Kaisha, Japan

[21] Appl. No.: 22,646

[22] Filed: Mar. 21, 1979

[30] Foreign Application Priority Data

Mar. 29, 1978 [JP] Japan .................................. 53-36483

[51] Int. Cl.³ .......................................... G01N 29/04
[52] U.S. Cl. .................................................. 73/626
[58] Field of Search ........................ 73/626, 607, 619; 367/11, 113; 128/660

[56] References Cited

U.S. PATENT DOCUMENTS

| 3,864,660 | 2/1975 | Ranalli et al. ........................ 367/11 |
| 4,024,490 | 5/1977 | Wood et al. .......................... 367/11 |
| 4,099,179 | 7/1978 | Hofstein ............................... 367/11 |
| 4,135,139 | 1/1979 | Buchner .............................. 73/626 |

OTHER PUBLICATIONS

Japanese Pat. Application No. 52-109781, 9/14/77.
Japanese Pat. Application No. 51-137344, 11/27/76.

*Primary Examiner*—Anthony V. Ciarlante
*Attorney, Agent, or Firm*—Finnegan, Henderson, Farabow, Garrett & Dunner

[57] ABSTRACT

An ultrasonic cross-sectional imaging apparatus comprising an ultrasonic probe, memory means and display means. The probe emits ultrasonic waves in non-interlaced fashion and receives echo data in non-interlaced fashion. The non-interlaced echo data are written into the memory means, read out therefrom in interlaced fashion and displayed by the display means as an image in interlaced fashion.

6 Claims, 4 Drawing Figures

ULTRASONIC CROSS-SECTIONAL IMAGING APPARATUS

BACKGROUND OF THE INVENTION

This invention relates to an ultrasonic cross-sectional imaging apparatus.

In the known ultrasonic cross-sectional imaging apparatus such as an ultrasonic diagnosis apparatus, both raster scanning of a display device and ultrasonic scanning are effected in interlaced fashion. That is, one frame is formed of two fields, and after a first field has been scanned, the second field is scanned along lines each extending between and parallel to the scanning lines of the first field. A time lag is inevitable between the scanning of the first field and that of the second field. Due to the time lag, images formed on the two fields are not completely superposed, particularly when a tomograph of a quickly moving object, e.g. the heart is taken. As a result, the resulting one-frame image is deformed.

Raster scanning of the display device and ultrasonic scanning may be carried out in non-interlaced fashion. In this case, however, a one-frame image is not so deformed as in interlaced fashion, but it would flicker since regions constituting one frame are sequentially scanned.

SUMMARY OF THE INVENTION

An object of this invention is to provide an ultrasonic cross-sectional imaging apparatus which can form an image being little deformed and never flickering.

According to this invention, there is provided an ultrasonic cross-sectional imaging apparatus wherein an image is formed in non-interlaced fashion, and an image information is temporarily stored in a memory and then read out therefrom to reproduce the image in interlaced fashion.

DETAILED DESCRIPTION OF THE PREFERRED EMBODIMENT

Figure 1:
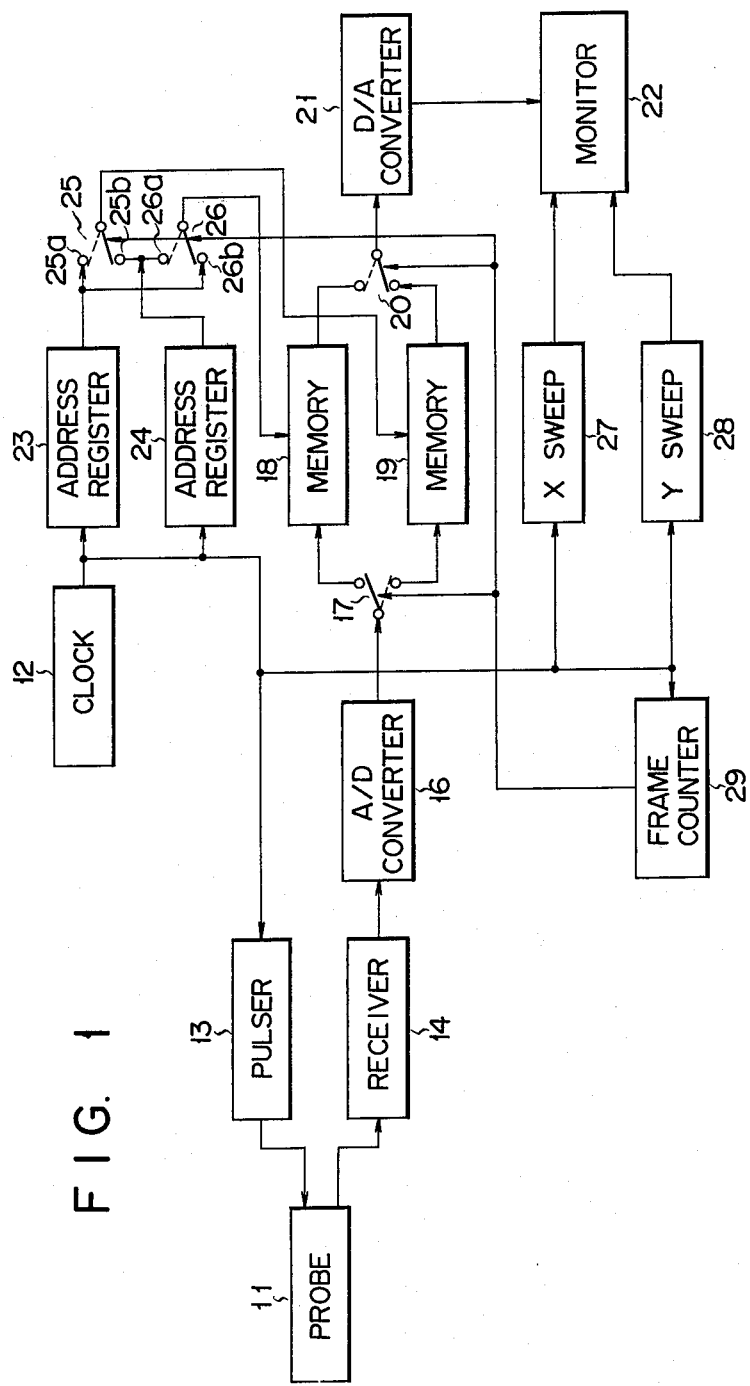
FIG. 1. is a block circuit diagram of an ultrasonic cross-sectional imaging apparatus according to an embodiment of this invention.

Now referring to FIG. 1, an ultrasonic cross-sectional imaging apparatus according to this invention will be described. The apparatus is provided with an ultrasonic probe 11 which is constituted by, for example, 64 electro-mechanical elements such as piexoelectric elements arranged in line. The probe 11 is connected to a pulser 13 and a receiver 14. The pulser 13, which is driven by clock pulses from a clock generator 12, is connected via an A/D converter 16 to a common terminal of a switch 17 which is constituted by, for example, an electronic switch element. Both contacts of the switch 17 are connected to memories 18 and 19, respectively. The read-out terminals of the memories 18 and 19 are connected to contacts of a switch 20, respectively. The common terminal of the switch 20 is connected via a D/A converter 21 to a monitor 22. The clock generator 12 supplies clock pulses to address registers 23 and 24, too. The output terminal of the address register 23 is connected to one contact 25a of an electronic switch 25 and one contact 26b of an electronic switch 26. The output terminal of the address register 24 is connected to the other contact 25b of the switch 25 and the other contact 26a of the switch 26. The common contacts of these switches 25 and 26 are connected to an address input terminal of the memory 18 and an address input terminal of the memory 19, respectively. The clock generator 12 supplies clock pulses also to an X sweeper 27, a Y sweeper 28 and a frame counter 29. The frame counter 29 counts clock pulses and produces an output signal every time its count reaches a predetermined value.

Figure 2:
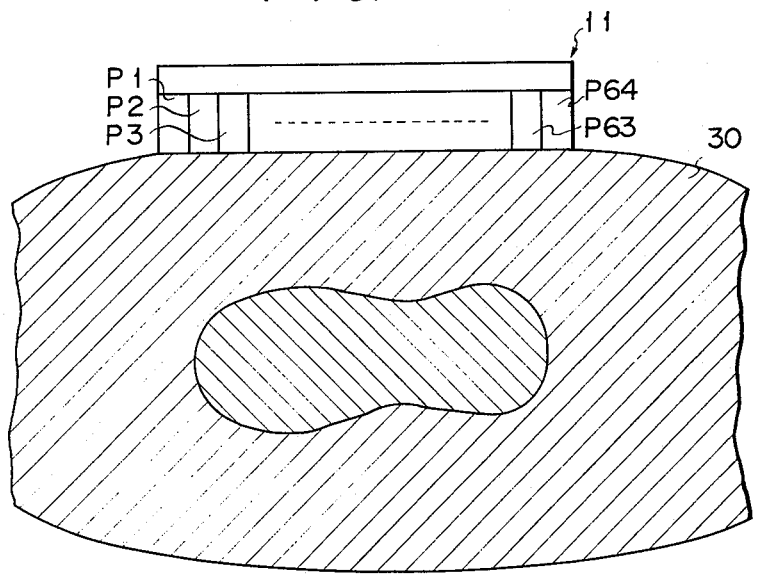
FIG. 2 shows a positional relationship between an object and an ultrasonic probe.
Figure 3:
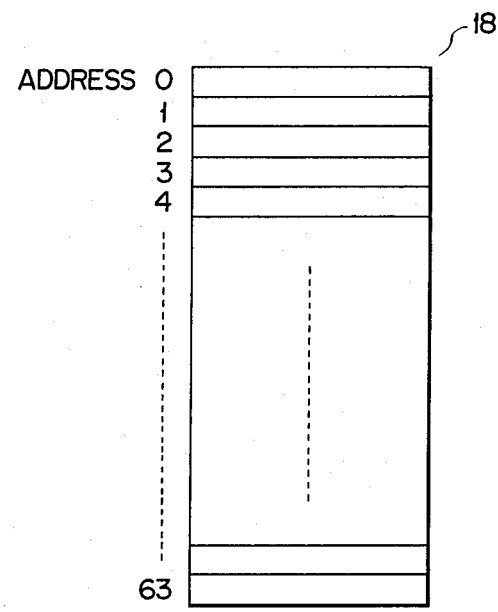
FIG. 3 illustrates the memories of the apparatus shown in FIG. 1.
Figure 3:
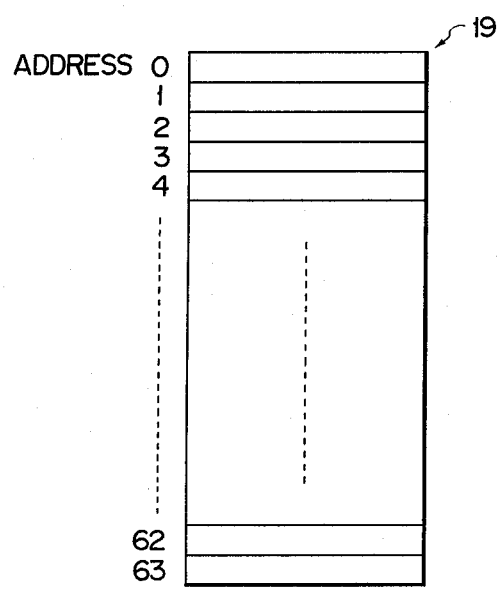

Now referring to FIGS. 2, 3 and 4, it will be described how the above-described ultrasonic cross-sectional imaging apparatus does operates. The probe 11 is put on an object 30 as illustrated in FIG. 2. The probe 11 in this position receives drive pulses generated by the pulser 13 in synchronism with clock pulses from the clock generator 12, whereby the piexoelectric elements P1 to P64 are sequentially driven to generates ultrasonic waves. The ultrasonic wave from each piezoelectric element is reflected from interfaces within the object 30. The reflected ultrasonic wave, i.e. echo, is received by the piezoelectric element and converted by the same into an electric signal (hereinafter called "echo signal"). The echo signal is supplied to the receiver 14 and amplified thereby. The amplified echo signal is then converted by the A/D converter 16 into a digital signal, which is supplied via the electronic switch 17 and then stored into the memory 18 as an echo data.

The echo data is constituted by, for instance, 260 bits in case the object 30 lies 260 mm deep, each bit being allocated to 1.0 mm. The echo data which have been obtained by the piezoelectric elements P1 to P64 in the above-mentioned manner are sequentially stored into the addresses 0 to 63 of the memory 18, respectively, which have been designated by non-interlace address data from the address register 23, as illustrated in FIG. 3. When all the addresses of the memory 18 are filled, the frame counter 29 produces an output signal. The output signal of the frame counter 29 operates the electronic switches 17, 20, 25 and 26 as indicated in dotted lines in FIG. 1. Once these switches have been so operated, the even-numbered addresses 0, 2, 4, 6, . . . 62 are sequentially designated by interlace address data from the address register 24, and then the odd-numbered addresses 1, 3, 5, . . . 63 are sequentially designated by interlace address data from the address register 24. As a result, the echo data are read out from the even-numbered addresses and then from the odd-numbered addresses of the memory 18, one after another. The echo data from the memory 18 are converted by the D/A converter 21 into analogue signals. The analogue signals are supplied to the monitor television 22, thereby forming an echo image on the screen of the monitor television 22.

When all the addresses of the memory 18 are filled up, new echo data coming from the probe 11 via the receiver 14, the addresses 0 to 63 of the memory 19 are designated by the non-interlace address data from the address register 23. Thus, new echo data coming from the probe 11 via the receiver 14 and the A/D converter 16 are sequentially written into the addresses 0 to 63 of the memory 19 via the electronic switch 17. When all the addresses of the memory 18 are emptied and all the addresses of the memory 19 are filled up, the frame counter 29 produces an output signal. The output signal of the counter 29 operates the electronic switches 17, 20, 25 and 26 as indicated in solid line in FIG. 1. Once these switches have been so operated, the even-numbered addresses of the memory 19 are sequentially designated by interlace address data from the address register 24, and then the odd-numbered addresses of the memory 19 are sequentially designated by the interlace address data from the address register 24. As a result the echo data are read out from the even-numbered addresses and then from the odd-numbered addresses of the memory 19, one after another. The echo data from the memory 19 are converted by the A/D converter 21 into analogue signals. The analogue signals are supplied to the monitor television 22, thereby forming an echo image on the screen of the monitor television 22.

Figure 4:
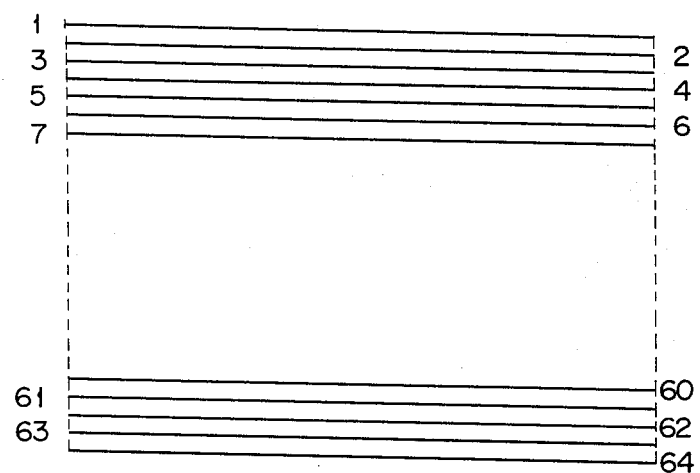
FIG. 4 shows scanning lines on the monitor television screen of the apparatus shown in FIG. 1.

As illustrated in FIG. 4, each of the scanning lines on the screen of the monitor television 22 correspond to a 260-bit echo data. More specifically, the echo data read out from the even-numbered addresses of the memory 18 or 19 correspond to the scanning lines 1, 3, 5, . . . 63, respectively, and the echo data read out from the odd-numbered addresses of the memory 18 or 19 correspond to the scanning lines 0, 2, 4, 6, . . . 64, respectively. Thus, the odd-numbered scanning lines constitute an odd line interlaced scanning field, and the even-numbered scanning lines an even line interlaced scanning field. In short, the echo data corresponding to the scanning lines 1 to 64 are sequentially written into the memory 18 or 19, but the echo data corresponding to the odd-numbered scanning lines are read out after those corresponding to the even-numbered scanning lines have been read out from the memory 18 or 19.

As the above-described data writing and reading are repeated, tomographs of the object 30 are displayed on the monitor television 22 one after another.

As mentioned above, an object 30 is scanned with the ultrasonic waves from the probe 11 by non-interlaced system, echo data obtained by the non-interlaced scanning are stored in a memory, and the screen of a monior television is scanned with the echo data from the memory in interlaced fashion thereby to display a tomograph of the object. Thus, the images formed by this method are little deformed and never flickering, even if the object moves quickly. The above-described apparatus can therefore obtain a clear-cut ultrasonic echo image, i.e. tomograph of a quickly moving object such as the heart. The image thus obtained can be observed on a monitor television and can be photographed.

In the above-described embodiment, the probe 11 is constituted by 64 piezoelectric elements, and 64 scanning lines are used. Instead, more or less piezoelectric elements may be used to constitute the probe 11, and more or less scanning lines may be used. Further, as mentioned above, each memory alternately stores and reads echo data thereby to form a one-frame image on the monitor television 22. Instead, each memory may repeatedly reads the same echo data so that a still image is formed on the monitor television. This can be achieved by, for example, preventing the frame counter 29 from supplying its output signal. Still further, in the above-described embodiment a linear ultrasonic scanning is employed. The scanning need not be limited to this method, and other scanning methods such as sector ultrasonic scanning can be employed, too. In the embodiment, echo data are written into the memories 18 and 19 in non-interlaced fashion. Instead, they may be written in interlaced fashion. If this is the case, the address register 23 supplies interlace address data.

What is claimed is:

1. An ultrasonic diagnostic apparatus for providing a cross-sectional image of an object comprising:
   ultrasonic probe means for emitting ultrasonic waves in a non-interlaced fashion and for producing frames of non-interlaced image data corresponding to the ultrasonic signal received;
   memory means interconnected with said ultrasonic probe means for storing the non-interlaced image data therefrom, said memory means having two memory sections capable of alternately storing either the immediate frame of image data being produced by said ultrasonic probe means or the preceding frame of image data produced;
   address means interconnected with said memory means and said probe means for writing in the image data corresponding to said immediate frame in a non-interlaced fashion in one of said memory sections and for simultaneously reading out of the other of said memory sections the image data corresponding to said preceding frame in an interlaced fashion; and
   image display means interconnected with said memory means for displaying the frame of interlaced image data read out from said memory means.

2. The ultrasonic apparatus of claim 1 further comprising:
   a clock generator means for supplying timed, sequential pulses to said electrical pulse generating means and said address means, and
   a control means responsive to said clock generator means for controlling the write in and read out operations of said address means so that only one frame of information is written in or read out from one of said memory sections at any one time.

3. An ultrasonic diagnostic apparatus for providing a cross-sectional image of an object on a raster scan display comprising:
   an electrical pulse generating means;
   an ultrasonic probe including a plurality of ultrasonic transducers responsive to said electrical pulse generating means to produce ultrasonic pulses in a non-interlaced fashion and produce frames of non-interlaced image data corresponding to the non-interlaced ultrasonic signals received;
   memory means interconnected with said ultrasonic probe for storing the non-interlaced image data therefrom, said memory means having two memory sections capable of alternately storing either the immediate frame of image data being produced by said ultrasonic probe means or the preceding frame of image data produced;
   address means interconnected with said memory means and said probe means for writing in the image data corresponding to said immediate frame in a non-interlaced fashion in one of said memory sections and for simultaneously reading out of the other of said memory sections the image data corresponding to said preceding frame in an interlaced fashion; and
   image display means interconnected with said memory means for displaying the frame of interlaced image data read out from said memory means in interlaced raster scan fashion.

4. The ultrasonic apparatus of claim 3 wherein:

each of said two memory sections includes a plurality of addresses, which plurality is at least equal to the number of transducers in said probe; and said address means includes an interlaced address register and a non-interlaced address register which are alternately connected to said memory sections to store the image data in interlaced fashion and read out the image data in non-interlaced fashion, respectively.

5. The ultrasonic diagnostic apparatus of claim 3 further comprising:

a clock generator means for supplying timed, sequential pulses to said electrical pulse generating means and said address means, and a controlmeans responsive to said clock generator means for controlling the write in and read out operations of said address means so that only one frame of information is written in or read out from one of said memory sections at any one time.

6. The ultrasonic diagnostic apparatus of claim 5 wherein:

each of said two memory sections includes a plurality of addresses, which plurality is at least equal to the number of transducers in said probe; and said address means includes an interlaced address register and a non-interlaced address register which are alternately connected to said memory sections to store the image data in interlaced fashion and read out the image data in non-interlaced fashion, respectively.

* * * * *